US009989506B2

(12) United States Patent
Watanabe et al.

(10) Patent No.: US 9,989,506 B2
(45) Date of Patent: Jun. 5, 2018

(54) GAS SENSOR AND GAS SENSOR MANUFACTURING METHOD

(71) Applicant: NGK INSULATORS, LTD., Nagoya-shi, Aichi (JP)

(72) Inventors: Yusuke Watanabe, Nagoya (JP); Takao Murase, Konan (JP); Masashi Yasui, Nagoya (JP)

(73) Assignee: NGK INSULATORS, LTD., Nagoya (JP)

(*) Notice: Subject to any disclaimer, the term of this patent is extended or adjusted under 35 U.S.C. 154(b) by 23 days.

(21) Appl. No.: 15/241,378

(22) Filed: Aug. 19, 2016

(65) Prior Publication Data
US 2017/0059540 A1   Mar. 2, 2017

(30) Foreign Application Priority Data

Aug. 25, 2015  (JP) ................................. 2015-165724

(51) Int. Cl.
*G01N 33/00* (2006.01)
*G01N 27/407* (2006.01)
*G01N 27/411* (2006.01)

(52) U.S. Cl.
CPC ..... *G01N 33/0027* (2013.01); *G01N 27/4077* (2013.01); *G01N 27/4118* (2013.01)

(58) Field of Classification Search
CPC .......... G01N 27/4077; G01N 27/4118; G01N 33/0027
See application file for complete search history.

(56) References Cited

U.S. PATENT DOCUMENTS

| 6,214,186 B1* | 4/2001 | Watanabe | G01N 27/4077 204/427 |
| 6,342,141 B1* | 1/2002 | Nelson | G01N 27/4077 204/424 |
| 6,945,091 B2* | 9/2005 | Nakagawa | G01N 27/4077 204/424 |
| 7,686,932 B2 | 3/2010 | Nishio et al. | |
| 9,354,215 B2* | 5/2016 | Schaefer | G01N 33/0027 |
| 2014/0190829 A1* | 7/2014 | Tabuchi | G01N 27/4077 204/431 |
| 2017/0010235 A1* | 1/2017 | Nakamura | G01N 27/409 |

FOREIGN PATENT DOCUMENTS

| JP | 3867423 B2 | 10/2006 |
| JP | 4387277 B2 | 10/2009 |

* cited by examiner

*Primary Examiner* — Lisa Caputo
*Assistant Examiner* — Punam Roy
(74) *Attorney, Agent, or Firm* — Global IP Counselors, LLP

(57) ABSTRACT

Provided is a gas sensor in which a protective cover has no looseness even by repetitive use. The gas sensor includes a sensor element for detecting a predetermined measurement target gas component in a measurement gas; a protective cover which protects a side of one end portion of the sensor element; and a housing which houses the sensor element. The protective cover includes a brim portion at one end portion of an outer surface of the protective cover. The brim portion is brought into contact with a contact surface provided in said housing, and is held between a swaging portion and the contact surface, the swaging portion extending from the contact surface while bending, so that the protective cover is fixed to the housing. The brim portion is tilted at a tilt angle of 5° or more and 15° or less relative to a plane vertical to a central axis of the gas sensor.

16 Claims, 5 Drawing Sheets

GAS SENSOR AND GAS SENSOR MANUFACTURING METHOD

BACKGROUND OF THE INVENTION

Field of the Invention

The present invention relates to a gas sensor for detecting a measurement gas by a sensor element, and particularly, to fixing of a protective cover which protects a sensor element in a gas sensor.

Description of the Background Art

Examples of gas sensors for detecting a predetermined gas component in a measurement gas such as an exhaust gas and obtaining a concentration thereof include various types such as a semiconductor type, a catalytic combustion type, an oxygen concentration difference detecting type, a limiting current type and a mixed potential type. Among these, some sensor elements include ceramic, which is a solid electrolyte such as zirconia, as a main constituent material.

Such a gas sensor commonly adopts a configuration in which a circumference of a sensor element is covered with a metallic protective member referred to as a protective cover or a protective cap (hereinafter, representatively referred to as a protective cover) for protecting the sensor element from being damaged or the like (see, e.g., Japanese Patent No. 3867423 and Japanese Patent No. 4387277).

A protective cover is generally fixed to a housing which houses a sensor element and other members, and such fixing is realized in a manner that a protrusion portion, also referred to as a brim portion, a flange portion or the like, which is provided on one end portion of an outer surface of a protective cover is fixed by swaging at a to-be-fixed part such as a swaging portion provided in the housing.

In a case where a gas sensor whose brim portion of a protective cover is fixed by swaging with a swaging portion of a housing is used for measuring a gas concentration in an exhaust pipe of an engine, thermal expansion due to heat of an exhaust gas and vibration of the engine may cause the protective cover to loosen in some cases.

Earnest investigation by the inventor has obtained findings that the looseness is caused by a configuration in which a brim portion of a protective cover protrudes in a direction perpendicular to an axis of a gas sensor.

SUMMARY OF THE INVENTION

The present invention relates to a gas sensor which detects a predetermined gas component as a measurement target in a measurement gas by means of a sensor element, and particularly, to fixing of a protective cover which protects a sensor element in a gas sensor.

According to the present invention, a gas sensor includes: a sensor element for detecting a predetermined measurement target gas component in a measurement gas; a protective cover which protects a side of one end portion of the sensor element; and a housing which houses the sensor element, in which the protective cover includes a brim portion at one end portion of an outer surface. The brim portion is brought into contact with a contact surface provided in the housing, and is held between a swaging portion and the contact surface, the swaging portion extending from the contact surface while bending, so that the protective cover is fixed to the housing. The brim portion is tilted at a tilt angle of 5° or more and 15° or less relative to a plane vertical to a central axis of the gas sensor.

Further, according to the present invention, provided is a method of manufacturing a gas sensor including a sensor element for detecting a predetermined measurement target gas component in a measurement gas, the method including the steps of: a) bringing a brim portion provided at one end portion of an outer surface of a protective cover which protects a side of one end portion of the sensor element into contact with a contact surface provided in a housing which houses the sensor element; and b) in a state where the brim portion is in contact with the contact surface by the step a), bending a swaging portion which extends from the contact surface in the housing to hold the brim portion between the swaging portion and the contact surface, so that the protective cover and the housing are fixed. The brim portion after being subjected to at least the step b) is tilted at a tilt angle of 5° or more and 15° or less relative to a plane vertical to a central axis of the gas sensor.

According to the present invention, even when the gas sensor is used repeatedly, fixing between the protective cover and the housing is realized by a fixing force sufficient for practical use which hardly causes looseness at the fixing part.

Accordingly, an object of the present invention is to provide a gas sensor in which a protective cover has no looseness even by repetitive use.

These and other objects, features, aspects and advantages of the present invention will become more apparent from the following detailed description of the present invention when taken in conjunction with the accompanying drawings.

DESCRIPTION OF THE PREFERRED EMBODIMENTS

<Configuration of Gas Sensor>

Figure 1:
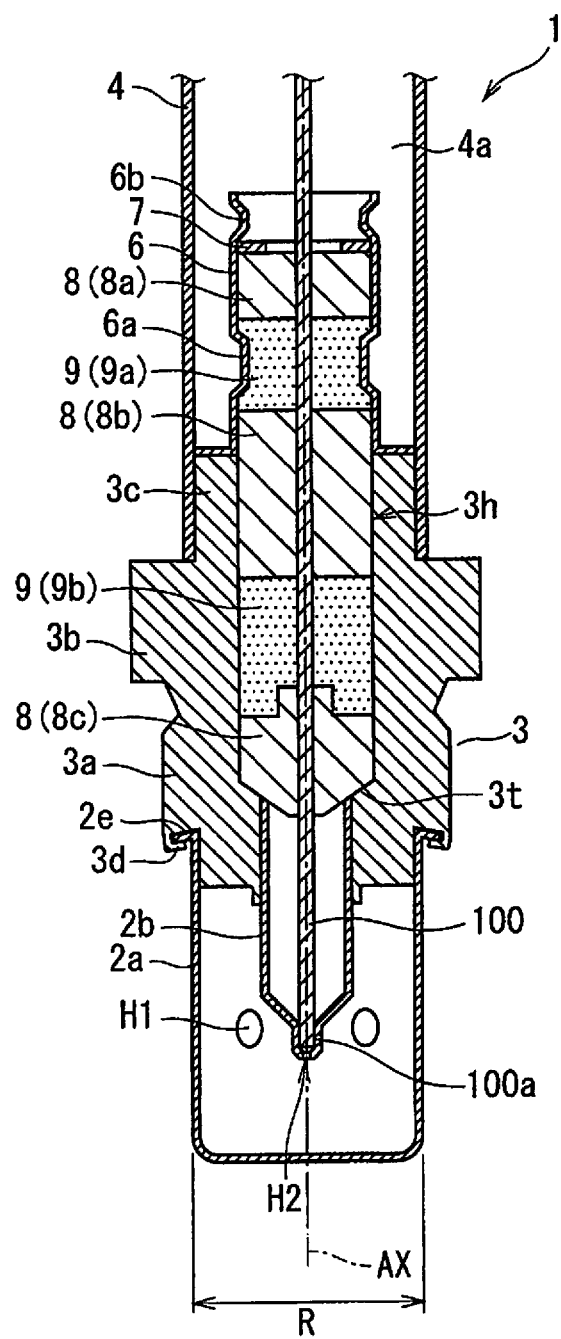
FIG. 1 is a partial sectional view showing a main configuration of a gas sensor 1.

FIG. 1 is a partial sectional view showing a main configuration of a gas sensor 1 (to be more strictly, a main body thereof) according to the present preferred embodiment. In the present preferred embodiment, the gas sensor 1 is for detecting a predetermined measurement target gas component (e.g. NOx or the like) in a measurement gas by means of a sensor element 100 provided therein. The sensor element 100 is a long pillar-shaped, thin-plate-shaped, cylindrical or tubular member having, as a main constituent material, an element body made of oxygen ion conducting solid electrolyte ceramic such as zirconia. In outline, the gas sensor 1 is configured to obtain a concentration of a measurement target gas component on the basis of a potential difference between an electrode in contact with a measurement gas and an electrode in contact with a reference gas (atmosphere) which are provided at an appropriate part of the sensor element 100, or on the basis of a volume of current flowing between both of the electrodes.

In FIG. 1 and the subsequent figures, the gas sensor 1 is shown in a manner in which a central axis (axis line) AX of a main body portion of the gas sensor 1 corresponds to an up-down direction in the figures, and unless otherwise noted, a lower side or a lower end side as viewed in the drawings will be referred to as a lower part or a lower end of each portion of the gas sensor 1 and an upper side or an upper end side as viewed in the drawings will be referred to as an upper part or an upper end of each portion of the gas sensor 1.

An outer part of the gas sensor 1 is mainly configured by a protective cover 2a, a housing 3, and an outer tube 4.

The protective cover 2a is a substantially cylindrical exterior member made of metal which protects an element end portion 100a and its vicinity. The element end portion 100a is a lowermost portion of the sensor element 100 in FIG. 1 and is a portion that comes into direct contact with a measurement gas when used.

The protective cover 2a is configured to be cylindrical and have a bottom at one side, and is also provided with a plurality of through holes, through which air can pass, at a side portion. While FIG. 1 shows a manner in which the protective cover 2a includes a plurality of through holes H1, the manner of arrangement of the through holes H1 shown in FIG. 1 is for illustrative purpose only and an arrangement position and the number of through holes H1 to be arranged may be appropriately determined in consideration of a manner of an inflow of a measurement gas into the protective cover 2a.

The protective cover 2a is fixed to the housing 3 at an upper end portion of an outer surface thereof. Details of fixing of this protective cover 2a will be described later.

The gas sensor 1 shown in FIG. 1 is further provided with an inner cover 2b in an inner space of the protective cover 2a and in the vicinity of the element end portion 100a of the sensor element 100. In other words, the gas sensor 1 has a two-layer structure including the protective cover 2a and the inner cover 2b to protect the vicinity of the element end portion 100a. The inner cover 2b shown in FIG. 1 is connected at an upper end portion thereof to a bottom end portion of a housing portion 3h of the housing 3 and is configured to have a reduced diameter in the vicinity of the element end portion 100a, i.e., at a lower end portion, such that the element end portion 100a fits in the diameter-reducing part. The inner cover 2b is further provided with a through hole H2 at a lowermost end portion thereof. However, the configuration of the inner cover 2b is not limited thereto. Any other configuration may be adopted as long as protection of the element end portion 100a and inflow of a measurement gas into the vicinity of the element end portion 100a are suitably realized.

The housing 3 is a metallic member, which includes the cylindrical housing portion 3h that houses therein the sensor element 100 and the like, and is used when fixing the gas sensor 1 at a measurement position. The housing 3 includes a screw portion 3a whose outer circumference part is threaded and a hexagonal portion 3b to be rotated when screwing the screw portion 3a, in such a manner that the screw portion 3a and the hexagonal portion 3b both radially protrude. A part of the housing 3 above the hexagonal portion 3b is an annular mounting portion 3c on which the outer tube 4 is annularly mounted. The screw portion 3a is screwed with a nut provided at an attachment position of the gas sensor 1. For example, by screwing the screw portion 3a with a nut portion provided in an exhaust pipe of a vehicle, the gas sensor 1 is fixed to the exhaust pipe in such a manner that the side of the protective cover 2a is exposed to the inside of the exhaust pipe.

The outer tube 4 is a metallic cylindrical member, which is annularly mounted on the annular mounting portion 3c of the housing 3, and protects a part of the gas sensor 1 that is not in contact with a measurement gas. The outer tube 4 is fixed to the annular mounting portion 3c by press-fitting or welding.

An inner space 4a of the outer tube 4 is a reference gas existing space in which an air as a reference gas is present. In a state where the gas sensor 1 is attached to a piping or the like in which a measurement gas is present, such as an exhaust pipe of an engine, by the screw portion 3a of the housing 3, the inner space 4a is isolated from the piping or the like. However, the inner space 4a is not sealed airtight and the atmosphere is allowed to enter or exit from the inner space 4a of the outer tube 4 through an opening provided at an upper end portion (not shown) of the outer tube 4.

Inside the outer tube 4, an inner tube 6 as a metallic cylindrical member is provided. The inner tube 6 has one end portion thereof fixed by welding to an upper end portion of the annular mounting portion 3c of the housing 3. The housing portion 3h of the housing 3 and the inner tube 6 have the substantially same internal diameter and are coaxially connected. As a result, the housing portion 3h of the housing 3 and the inner tube 6 are continuous along the central axis AX to configure a tubular body having one cylindrical housing space.

Then, in such a housing space, the sensor element 100 is arranged such that a longitudinal direction is positioned on the central axis AX, and a washer 7, three ceramic supporters 8 (8a, 8b, 8c) and two powder compacts 9 (9a, 9b) are coaxially mounted annularly on the sensor element 100. The ceramic supporters 8 and the powder compacts 9 are alternately mounted annularly. In other words, in the gas sensor 1, with the sensor element 100 arranged on the central axis AX, the washer 7, the three ceramic supporters 8 (8a, 8b, 8c) and the two powder compacts 9 (9a, 9b) are annularly mounted along the central axis AX, and on the further outside, the housing portion 3h of the housing 3 and the inner tube 6, and further, the outer tube 4 are annularly mounted.

Here, the ceramic supporter 8 is an insulator made of ceramic. On the other hand, the powder compact 9 is a molded product of ceramic powder such as talc. In the following description, the washer 7, the ceramic supporter 8 and the powder compact 9 may be collectively referred to as an annular mounting member.

More specifically, at one end inside the housing 3, a tapered portion 3t is provided, with which the washer 7, the ceramic supporters 8 (8a, 8b, 8c) and the powder compacts 9 (9a, 9b) which are annularly mounted on the sensor element 100 are engaged. This is realized by fitting a tubular body formed by the housing 3 and the inner tube 6 to outer circumferences of the annular mounting members, with the annular mounting members having been annularly mounted on the sensor element 100 in advance. With such engagement completed, a predetermined load is applied to the washer 7 from above to compress the powder compacts 9, so that the sensor element 100 is sealed between its both end portions within the tubular body. With such sealing completed, a position 6b immediately above the washer 7 is swaged from the outside, so that the annular mounting members are constrained to ensure airtightness between both the end portions of the sensor element 100. Further, a position 6a adjacent to the powder compact 9a in the inner tube 6 is swaged from the outside so as to ensure airtightness between both the end portions of the sensor element 100.

Although not shown in the figures, in the gas sensor 1, at a position within the outer tube 4 and above the inner tube 6, a connector for electric connection with the outside of the sensor element 100 is connected to a plurality of terminal electrodes provided in the sensor element 100, and a cable extending from the connector is drawn from an opening which is also an air inlet and outlet provided in the upper end portion of the outer tube 4.

With such a configuration as described above, in the gas sensor 1 being attached at a predetermined position, a space where a measurement gas is existing around the element end portion 100a of the sensor element 100 and a space where a reference gas is existing around the other end portion are completely isolated from each other. This enables highly precise measurement of a concentration of a target gas component in a measurement gas.

<Fixing of Protective Cover>

Figure 2:
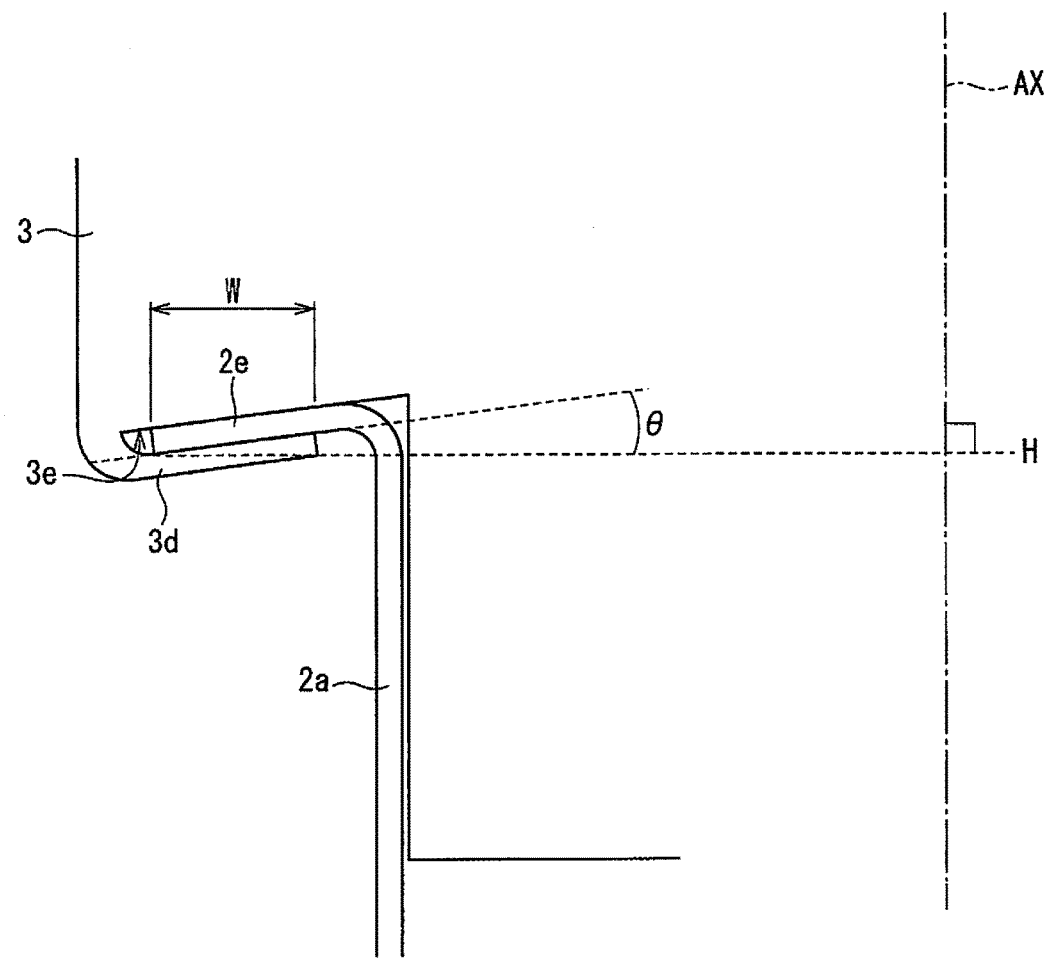
FIG. 2 is an enlarged sectional view schematically showing a fixing part between a protective cover 2a and a housing 3.
Figure 3:
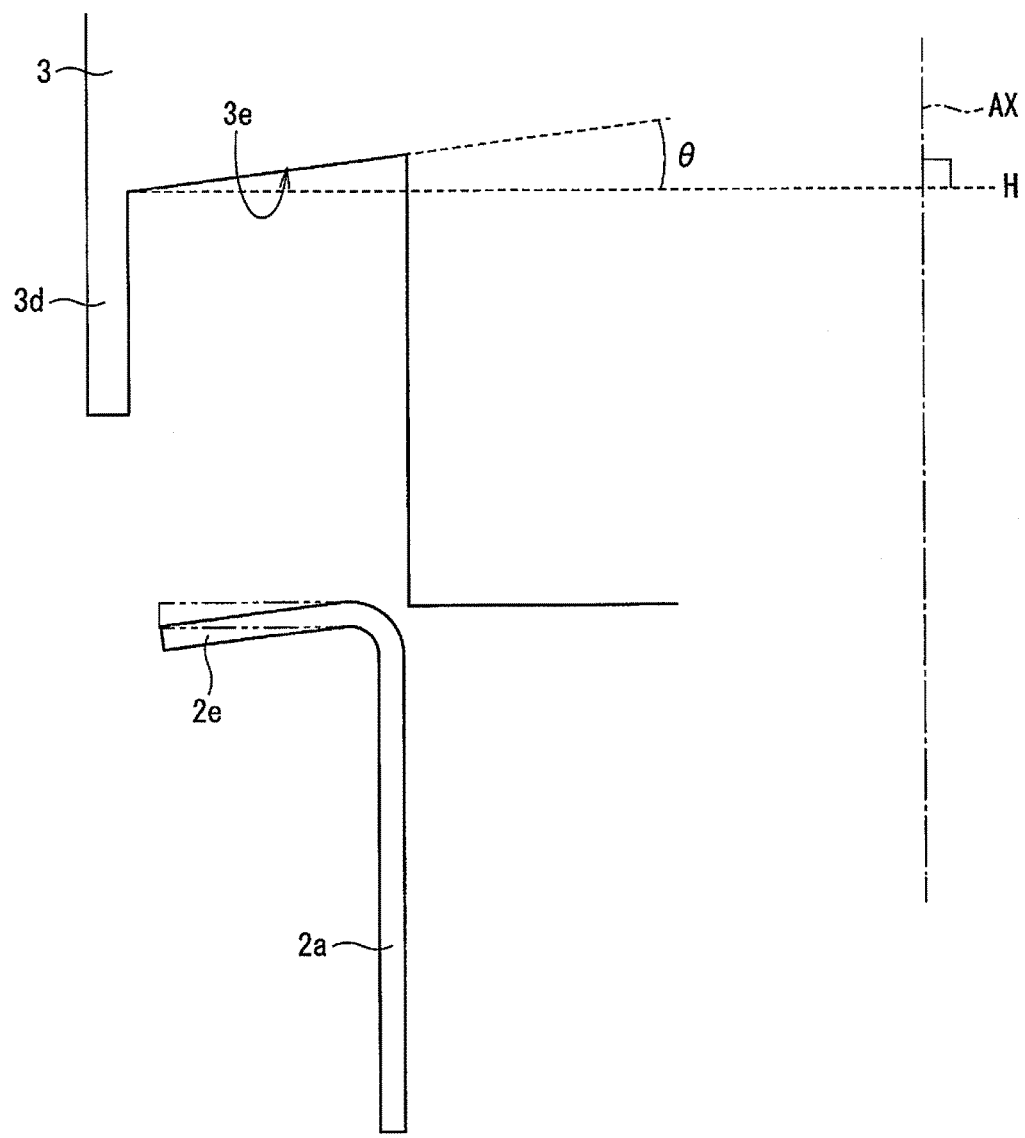
FIG. 3 is a view showing a state before the protective cover 2a is fixed to the housing 3.
Figure 4:
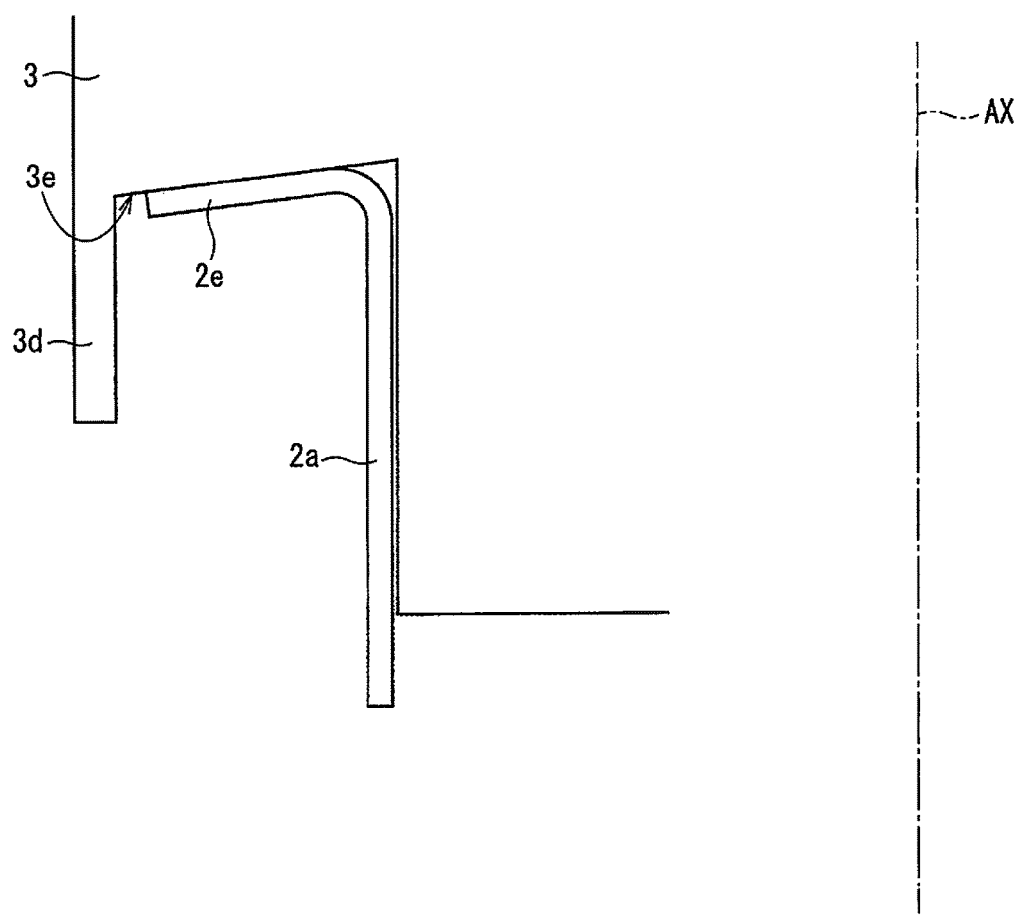
FIG. 4 is a view showing a state in the process of fixing the protective cover 2a to the housing 3.

Next, fixing of the protective cover 2a to the housing 3 will be described in detail. FIG. 2 is an enlarged sectional view schematically showing a fixing part between the protective cover 2a and the housing 3. FIG. 3 is a view showing a state before the protective cover 2a is fixed to the housing 3, and FIG. 4 is a view showing a state in the process of fixing the protective cover 2a to the housing 3.

As shown in FIG. 1 and FIG. 2, although the protective cover 2a is schematically cylindrical, at a part of the upper end of the outer surface thereof, a brim portion 2e is provided annularly along an outer circumference of the protective cover 2a in advance, the brim portion 2e being bent radially outward from a cylindrical part of the cover 2a. Schematically, owning to the hold of the brim portion 2e between a swaging portion 3d and a contact surface 3e of the housing 3, the protective cover 2a is fixed to the housing 3.

More specifically, in the housing 3, a lower end portion of the screw portion 3a which is radially protruding forms a plane over an entire outer circumference of the housing 3, which implements the provision of the annular contact surface 3e. This contact surface 3e, as shown in FIG. 3, is disposed to tilt relative to a plane H orthogonal to the central axis AX (parallel to the longitudinal direction of the gas sensor 1), such that an inner side thereof in the radial direction is located higher in the direction of the central axis AX (the closer to the central axis AX, the farther from the element end portion 100a of the sensor element 100, in the direction of the central axis AX). In this case, with a direction from the outside to the inside in the radial direction on the plane H as a reference position (a position at 0°), a tilt angle θ is 5°≤θ≤15° when a counterclockwise direction is assumed to be a positive direction.

On the other hand, the swaging portion 3d is in parallel to the central axis AX before fixing of the protective cover 2a as shown in FIG. 3. When fixing the protective cover 2a, after housing the sensor element 100 and the like into the housing portion 3h, the brim portion 2e of the protective cover 2a is brought into contact with the contact surface 3e as shown in FIG. 4. Then, when the swaging portion 3d is thereafter swaged (bent) by swaging means (not shown), the brim portion 2e is held by the swaging portion 3d and the contact surface 3e. This realizes a state where the protective cover 2a is fixed to the housing 3. In such a state, as shown in FIG. 2, the brim portion 2e provided at the upper end portion of the outer surface of the protective cover 2a is also tilted at the tilt angle of 5°≤θ≤15° relative to the plane H so as to follow such a tilt of the contact surface 3e (the closer to the central axis AX, the farther from the element end portion 100a of the sensor element 100, in the direction of the central axis AX).

With the brim portion 2e thus tilted, fixing the protective cover 2a to the housing 3 by swaging results in having larger frictional resistances between the brim portion 2e, and the swaging portion 3d and the contact surface 3e, respectively, in the gas sensor 1, as compared to a case of (0°≤) θ≤5° (typically, in a case of no tilt). This realizes fixing with a large fixing force, to the extent that the fixing part hardly loosens even when repetitive vibration, or thermal expansion/thermal contraction occurs due to use of the gas sensor 1. For example, when θ=0°, thermal expansion easily occurs in a horizontal direction in which no other force than a frictional force acts, thermal expansion in the present preferred embodiment occurs in different directions, resulting in that the protective cover 2a hardly loosens.

At θ>15°, when the brim portion 2e of the protective cover 2a is brought into contact with the contact surface 3e and further and then the swaging portion 3d is swaged, cracks are generated at bent parts of the brim portion 2e and the swaging portion 3d. It is undesirable.

The brim portion 2e of the protective cover 2a before being brought into contact with the contact surface 3e is not required to tilt at the same tilt angle θ as that of the contact surface 3e and may, for example, be parallel to the plane H as indicated by chain double-dashed lines in FIG. 3 or be tilted at other angle.

Additionally, both the brim portion 2e and the contact surface 3e are not required to be completely annular, and as long as a sufficient fixing force is ensured between the protective cover 2a and the housing 3, both the brim portion 2e and the contact surface 3e may be intermittently provided in a circumferential direction of the protective cover 2a or the housing 3.

A width W (FIG. 2) in a radial direction of an overlapping part between the brim portion 2e and the swaging portion 3d after swaging is preferably at least 10% or more of a diameter R (FIG. 1) of the cylindrical part of the protective cover 2a. In such a case, the protective cover 2a is less likely to loosen. The diameter R is generally on the order of 10 mm to 15 mm and in such a case, setting the width W to be on the order of 1 mm to 1.5 mm or more enables the protective cover 2a to be fixed to the housing 3 so as to cause no looseness. Theoretically, the width W may be as large as it could be, but actually, an upper limit value of the width W is determined based on a size required for the swaging portion 3d or other part.

<Another Manner of Fixing Protective Cover>

Figure 5:
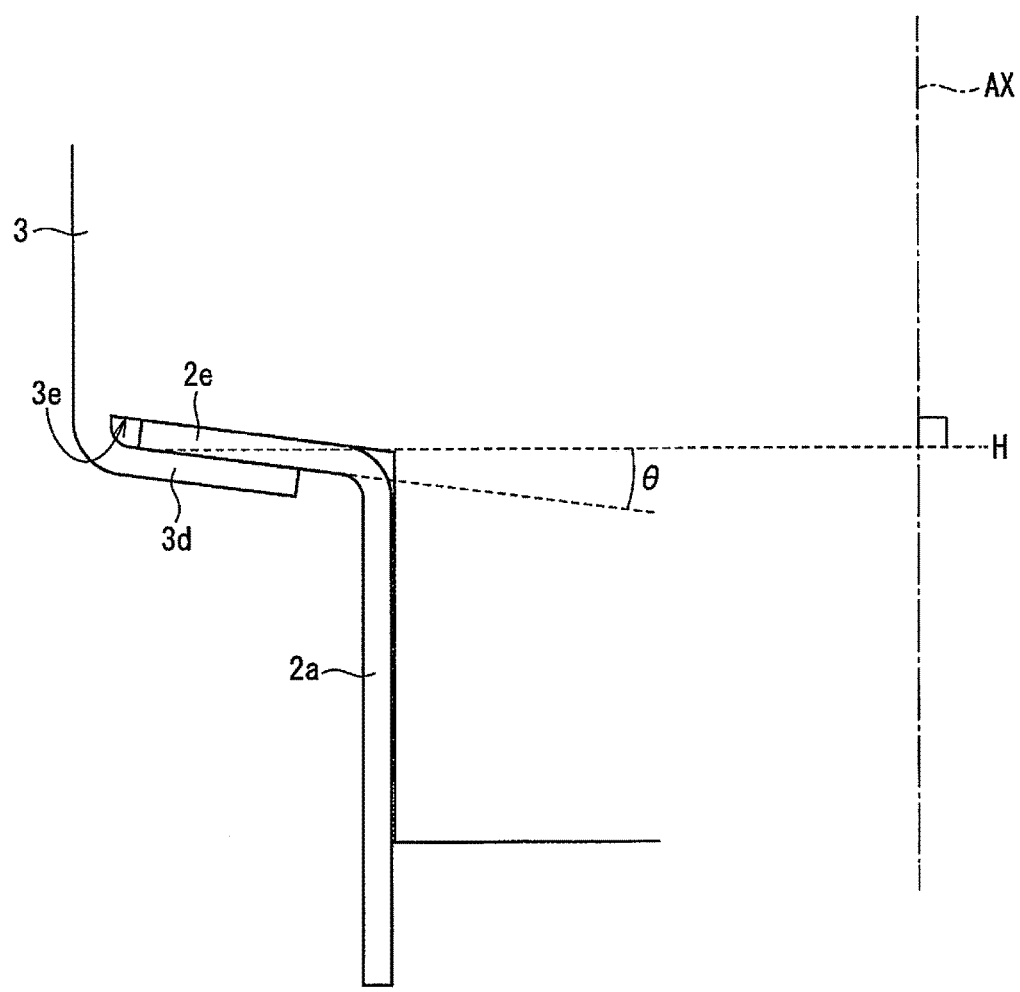
FIG. 5 is an enlarged sectional view schematically showing a fixing part between the protective cover 2a and the housing 3, which shows another manner of tilting a brim portion 2e.

While FIG. 1 to FIG. 4 show a manner of tilting the brim portion 2e at the tilt angle θ of 5°≤θ≤15° such that its inner side in the radial direction is located higher in the direction of the central axis AX so as to fix the protective cover 2a to the housing 3 by swaging, the manner of fixing the protective cover 2a to the housing 3 by tilting the brim portion 2e is not limited thereto. FIG. 5 is an enlarged sectional view schematically showing the fixing part between the protective cover 2a and the housing 3, which shows another manner of tilting the brim portion 2e.

In the manner shown in FIG. 5, the contact surface 3e is disposed to tilt relative to the plane H orthogonal to the central axis AX, such that the inner side thereof in the radial direction is located lower in the direction of the central axis AX (the closer to the central axis AX, the closer to the element end portion 100a of the sensor element 100, in the direction of the central axis AX). Here, the tilt angle is −15°≤θ≤−5°. The brim portion 2e provided at the upper end portion of the outer surface of the protective cover 2a is also tilted at the tilt angle θ of −15°≤θ≤−5° relative to the plane H so as to follow such a tilt of the contact surface 3e (the closer to the central axis AX, the closer to the element end portion 100a of the sensor element 100, in the direction of the central axis AX). In other words, tilt directions of the contact surface 3e and the brim portion 2e are reverse to those in the manner shown in FIG. 2.

With the brim portion 2e tilted in such a manner, fixing the protective cover 2a to the housing 3 by swaging results in having larger frictional resistances between the brim portion 2e, and the swaging portion 3d and the contact surface 3e, respectively, in the gas sensor 1 as compared to a case of −5°<θ (≤0°) (typically, in a case of no tilt). Also in this case, similarly to the above case of 5°≤θ≤15°, fixing with a large fixing force can be realized, to the extent that the fixing part hardly loosens even when repetitive vibration, or thermal expansion/thermal contraction occurs due to use of the gas sensor 1. At −15°<θ, the protective cover 2a is undesirably likely to loosen.

Also in a case of fixing in the manner as shown in FIG. 5, the width in the radial direction of the overlapping part between the brim portion 2e and the swaging portion 3d after swaging is preferably 10% or more of the diameter of the cylindrical part of the protective cover 2a.

Putting the manner shown in FIG. 2 and the manner shown in FIG. 5 into consideration, the protective cover 2a is fixed to the housing 3 with a fixing force sufficient in practical use as long as the tilt angles of the contact surface 3e of the housing 3 and the brim portion 2e of the protective cover 2a relative to the plane H vertical to the central axis AX of the gas sensor 1 is 5° or more and 15° or less.

As described above, according to the present preferred embodiment, in the gas sensor, fixing between the protective cover, which protects the end portion side of the sensor element in contact with a measurement gas, and the housing which houses the sensor element is realized by swaging the swaging portion provided in the housing such that the brim portion provided at one end portion of the outer surface of the protective cover is held between the contact surface and the swaging portion. In this fixing, the brim portion is held between the contact surface and the swaging portion, with tilted at the tilt angle of 5° or more and 15° or less in either a positive or negative direction relative to the plane vertical to the central axis of the gas sensor due to following the contact surface. As a result, fixing with a fixing force sufficient in practical use can be realized, to the extent that the fixing part hardly loosens even when the gas sensor is repeatedly used. In such a case, since the tilt angle is suitably determined, no crack is generated in the brim portion and the swaging portion after repetitive use.

EXAMPLE

A total of 21 types of gas sensors 1 were prepared which have the tilt angle θ in a range of −20°≤θ≤20° and with respect to each sensor, in order to simulatively realize a state after repetitive use of the gas sensor 1, a heating vibration test was conducted to determine presence or absence of looseness at the protective cover 2a after the test, and presence or absence of generation of a crack in the brim portion 2e of the protective cover 2a and the swaging portion 3d of the housing 3. And then, with the comprehensive consideration of determination results thereof, a quality of a state of fixing by swaging the protective cover 2a to the housing 3 was determined.

The heating vibration test was conducted with the gas sensor 1 attached to an exhaust pipe of a propane burner installed in a vibration testing machine under the following conditions.

Gas temperature: 850° C.;
Vibration condition: sweep of 50 Hz→250 Hz→50 Hz conducted for 30 minutes;
Acceleration: 50 G;
Test time: 150 hours.

In Table 1, a value of the tilt angle θ in each gas sensor 1 and a determination result are shown. As to presence and absence of looseness at the protective cover 2a after the test, determination was made based on a criterion that when a force is applied in a circumferential direction of the protective cover 2a manually by a tester, looseness is present if the protective cover 2a rotates in the circumferential direction, and no looseness is present if the protective cover 2a fails to rotate. In Table 1, "absence" is assigned when no looseness is present and "presence" is assigned when looseness is present. Additionally, determination of presence/absence of a crack was made by visually observing both the brim portion 2e of the protective cover 2a and the swaging portion 3d of the housing 3. In Table 1, "absence" is assigned when no crack was observed and "presence" is assigned when a crack was observed. Then, a quality of a state of fixing by swaging is determined to be satisfactory only when neither looseness nor a crack was observed, and determined to be unsatisfactory when at least one of looseness and a crack was observed. In Table 1, the former is indicated as "satisfactory" and the latter is indicated as "unsatisfactory".

TABLE 1

| θ(°) | Looseness | Presence/absence of cracks | Determination of swaging quality |
|---|---|---|---|
| −20 | Presence | Absence | Unsatisfactory |
| −17 | Presence | Absence | Unsatisfactory |
| −15 | Absence | Absence | Satisfactory |
| −13 | Absence | Absence | Satisfactory |
| −11 | Absence | Absence | Satisfactory |
| −9 | Absence | Absence | Satisfactory |
| −7 | Absence | Absence | Satisfactory |
| −5 | Absence | Absence | Satisfactory |
| −3 | Presence | Absence | Unsatisfactory |
| −1 | Presence | Absence | Unsatisfactory |
| 0 | Presence | Absence | Unsatisfactory |
| 1 | Presence | Absence | Unsatisfactory |
| 3 | Presence | Absence | Unsatisfactory |
| 5 | Absence | Absence | Satisfactory |
| 7 | Absence | Absence | Satisfactory |
| 9 | Absence | Absence | Satisfactory |
| 11 | Absence | Absence | Satisfactory |
| 13 | Absence | Absence | Satisfactory |
| 15 | Absence | Absence | Satisfactory |
| 17 | Absence | Presence | Unsatisfactory |
| 20 | Absence | Presence | Unsatisfactory |

As shown in Table 1, the gas sensors 1 with the tilt angle θ values in the range of −15°≤θ≤−5° and the range of 5°≤θ≤20° were determined to have no looseness in the protective cover 2a and other gas sensors 1 were determined to have looseness.

Additionally, cracks were observed only in the gas sensors 1 with the tilt angle θ values of 17° and 20°, and the other gas sensors 1 with the tilt angle θ values in the range of −20≤θ≤15° were determined to have no cracks.

From the foregoing results, the gas sensors 1 with the tilt angle θ values in the range of −15≤θ≤−5° and the range of 5°≤θ≤15° were determined in the heating vibration test that the protective cover 2a was satisfactorily fixed to the housing 3. Such a result indicates that in the gas sensors 1 with the tilt angle θ values in the range of −15°≤θ≤−5° and the range of 5°≤θ≤15°, a sufficient fixing force was ensured even after repetitive use so as to hardly cause looseness and generate no crack.

What is claimed is:

1. A gas sensor comprising:
a sensor element for detecting a predetermined measurement target gas component in a measurement gas;
a protective cover which protects one end portion side of said sensor element; and
a housing which houses said sensor element,
wherein said protective cover includes a brim portion at one end portion of an outer surface,
said brim portion is brought into contact with a contact surface provided in said housing, and is held between a swaging portion and said contact surface, said swaging portion extending from said contact surface while bending, so that said protective cover is fixed to said housing, and
said brim portion is tilted at a tilt angle of 5° or more and 15° or less relative to a plane vertical to a central axis of said gas sensor, wherein said brim portion is tilted so as to follow a tilt of said contact surface.

2. The gas sensor according to claim 1, wherein
said contact surface tilts at the tilt angle of 5° or more and 15° or less relative to said plane and said brim portion follows said contact surface to tilt.

3. The gas sensor according to claim 2, wherein
said brim portion is provided so as to be farther from said one end portion side of said sensor element in a direction of said central axis as said brim portion is closer to said central axis.

4. The gas sensor according to claim 3, wherein
said protective cover is cylindrical, and
a width of an overlapping part between said brim portion and said swaging portion in a radial direction of said protective cover is 10% or more of a diameter of a cylindrical part of said protective cover.

5. The gas sensor according to claim 2, wherein
said protective cover is cylindrical, and
a width of an overlapping part between said brim portion and said swaging portion in a radial direction of said protective cover is 10% or more of a diameter of a cylindrical part of said protective cover.

6. The gas sensor according to claim 1, wherein
said brim portion is provided so as to be farther from said one end portion side of said sensor element in a direction of said central axis as said brim portion is closer to said central axis.

7. The gas sensor according to claim 6, wherein
said protective cover is cylindrical, and
a width of an overlapping part between said brim portion and said swaging portion in a radial direction of said protective cover is 10% or more of a diameter of a cylindrical part of said protective cover.

8. The gas sensor according to claim 1, wherein
said protective cover is cylindrical, and
a width of an overlapping part between said brim portion and said swaging portion in a radial direction of said protective cover is 10% or more of a diameter of a cylindrical part of said protective cover.

9. A method of manufacturing a gas sensor including a sensor element for detecting a predetermined measurement target gas component in a measurement gas, the method comprising the steps of:

a) bringing a brim portion provided at one end portion of an outer surface of a protective cover which protects one end portion side of said sensor element into contact with a contact surface provided in a housing which houses said sensor element; and
b) in a state where said brim portion is in contact with said contact surface by said step a), bending a swaging portion which extends from said contact surface in said housing to hold said brim portion between said swaging portion and said contact surface, so that said protective cover and said housing are fixed, wherein
said brim portion after being subjected to at least said step b) is tilted at a tilt angle of 5° or more and 15° or less relative to a plane vertical to a central axis of said gas sensor and wherein said brim portion, after being subjected to at least step b), is tilted so as to follow a tilt of said contact surface.

10. The method of manufacturing a gas sensor according to claim 9, wherein
said contact surface tilts at the tilt angle of 5° or more and 15° or less relative to said plane and said brim portion follows said contact surface to tilt at said tilt angle in said contacting step.

11. The method of manufacturing a gas sensor according to claim 10, wherein
said brim portion is tilted so as to be farther from said one end portion side of said sensor element in a direction of said central axis as said brim portion is closer to said central axis.

12. The method of manufacturing a gas sensor according to claim 11, wherein
said protective cover is cylindrical, and
in said step b), said swaging portion is bent such that a width of an overlapping part between said brim portion and said swaging portion in a radial direction of said protective cover is 10% or more of a diameter of a cylindrical part of said protective cover.

13. The method of manufacturing a gas sensor according to claim 10, wherein
said protective cover is cylindrical, and
in said step b), said swaging portion is bent such that a width of an overlapping part between said brim portion and said swaging portion in a radial direction of said protective cover is 10% or more of a diameter of a cylindrical part of said protective cover.

14. The method of manufacturing a gas sensor according to claim 9, wherein
said brim portion is tilted so as to be farther from said one end portion side of said sensor element in a direction of said central axis as said brim portion is closer to said central axis.

15. The method of manufacturing a gas sensor according to claim 14, wherein
said protective cover is cylindrical, and
in said step b), said swaging portion is bent such that a width of an overlapping part between said brim portion and said swaging portion in a radial direction of said protective cover is 10% or more of a diameter of a cylindrical part of said protective cover.

16. The method of manufacturing a gas sensor according to claim 9, wherein
said protective cover is cylindrical, and
in said step b), said swaging portion is bent such that a width of an overlapping part between said brim portion and said swaging portion in a radial direction of said protective cover is 10% or more of a diameter of a cylindrical part of said protective cover.

* * * * *